United States Patent
Watanabe et al.

(10) Patent No.: US 9,741,127 B1
(45) Date of Patent: Aug. 22, 2017

(54) IMAGE PROCESSING DEVICE

(71) Applicant: SHIMADZU CORPORATION, Kyoto-shi, Kyoto (JP)

(72) Inventors: Shota Watanabe, Kyoto (JP); Tomonori Sakimoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 168 days.

(21) Appl. No.: 14/785,645

(22) PCT Filed: May 10, 2013

(86) PCT No.: PCT/JP2013/003016
§ 371 (c)(1),
(2) Date: Oct. 20, 2015

(87) PCT Pub. No.: WO2014/181383
PCT Pub. Date: Nov. 13, 2014

(51) Int. Cl.
*G06T 7/00* (2017.01)
*A61B 6/12* (2006.01)
(Continued)

(52) U.S. Cl.
CPC .............. *G06T 7/0083* (2013.01); *A61B 6/12* (2013.01); *G06T 5/009* (2013.01); *G06T 7/0093* (2013.01);
(Continued)

(58) Field of Classification Search
None
See application file for complete search history.

(56) References Cited

U.S. PATENT DOCUMENTS

| | | | |
|---|---|---|---|
| 6,426,988 B2 * | 7/2002 | Yamada | G06T 11/005 378/4 |
| 8,908,832 B2 | 12/2014 | Yamashita | |

(Continued)

FOREIGN PATENT DOCUMENTS

| | | |
|---|---|---|
| EP | 1 825 810 | 8/2007 |
| EP | 2 995 255 | 4/2017 |

(Continued)

OTHER PUBLICATIONS

U.S. Appl. No. 14/759,353, filed Jul. 6, 2015, Okuno.
(Continued)

*Primary Examiner* — Kim Vu
*Assistant Examiner* — Molly Delaney
(74) *Attorney, Agent, or Firm* — Andrew F. Young, Esq.; Lackenbach Siegel, LLP

(57) ABSTRACT

The image processing device generates an operation image by adding or subtracting an original image and a standard deviation image which maps the standard deviation for the pixels configuring the original image. In this operation image, images of the structures seen in parts in the original image other than metal pieces are erased. Consequently, structures that are not metal pieces appearing in the original image in a whitish color, for example, do not appear in the operation image. If such an operation image is subjected to binarization processing in which the metal pieces appearing in a whitish color, for example, are extracted, since accurate graph cut processing is then possible, images originating from structures that are not metal pieces do not appear in the resulting image.

3 Claims, 24 Drawing Sheets

(51) Int. Cl.
*G06T 5/00* (2006.01)
*G06T 11/00* (2006.01)

(52) U.S. Cl.
CPC .. *G06T 11/005* (2013.01); *G06T 2207/10081* (2013.01); *G06T 2207/20144* (2013.01); *G06T 2207/30008* (2013.01)

(56) References Cited

U.S. PATENT DOCUMENTS

| | | | |
|---|---|---|---|
| 8,983,029 | B2 | 3/2015 | Hasegawa |
| 9,125,619 | B2 | 9/2015 | Yabugami |

FOREIGN PATENT DOCUMENTS

| | | |
|---|---|---|
| JP | 2001-22916 | 1/2001 |
| JP | 2004-153298 | 5/2004 |
| JP | 2004-320701 | 11/2004 |
| JP | 2005-323926 | 11/2005 |
| JP | 2010099114 | 5/2010 |
| JP | 2011-28322 | 2/2011 |

OTHER PUBLICATIONS

U.S. Appl. No. 14/785,758, filed Oct. 20, 2015, Sakimoto.
U.S. Appl. No. 14/784,528, filed Oct. 24, 2015, Okuno.
U.S. Appl. No. 13/719,032, filed Dec. 18, 2012, Takahasi.
U.S. Appl. No. 13/995,872, filed Aug. 20, 2013, Kogame.
U.S. Appl. No. 14/157,120, filed Jan. 16, 2014, Okamura.
U.S. Appl. No. 14/363,345, filed Jul. 15, 2014, Ishikawa.
U.S. Appl. No. 14/416,412, filed Jan. 22, 2015, Ishikawa.
U.S. Appl. No. 14/668,354, filed Mar. 25, 2015, Tanaka.
U.S. Appl. No. 14/754,056, filed Jun. 29, 2015, Tanaka.
U.S. Appl. No. 14/760,152, filed Jul. 9, 2015, Tanaka.
U.S. Appl. No. 14/798,991, filed Jul. 14, 2015, Shirota.
U.S. Appl. No. 14/830,187, filed Aug. 19, 2015, Kawabe.
U.S. Appl. No. 14/764,018, filed Jul. 28, 2015, Kakio.
U.S. Appl. No. 14/785,737, filed Oct. 20, 2015, Watanabe.
U.S. Appl. No. 14/766,522, filed Aug. 7, 2015, Okuno.
PCT/JP2013/003016, International Search Report mailed Jul. 2, 2013, 3 pags—Japanese, 2 pages—English.
EP 13 884 130.9, Communication under Article 97(1) EPC, Decision to grant, dated Mar. 23, 2017, 1 pg. English.
EP 13 884 130.9, Communication under Rule 71(3) EPC, Intention to grant, dated Nov. 11, 2016, 7 pages—English.

\* cited by examiner

FIG. 7(A)
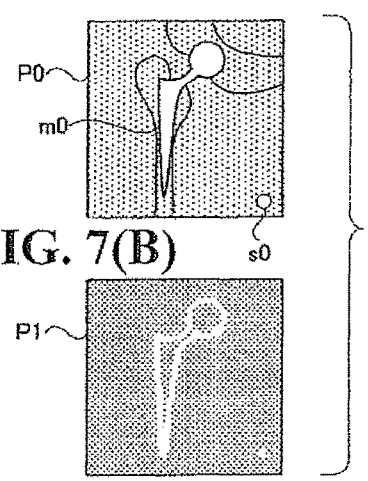
FIG. 7(B)
FIG. 7(C)
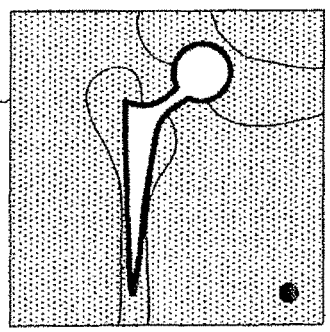

Obtain the representative value bg

Obtain the representative value obj

Exstraction Processing

FIG. 20(A)
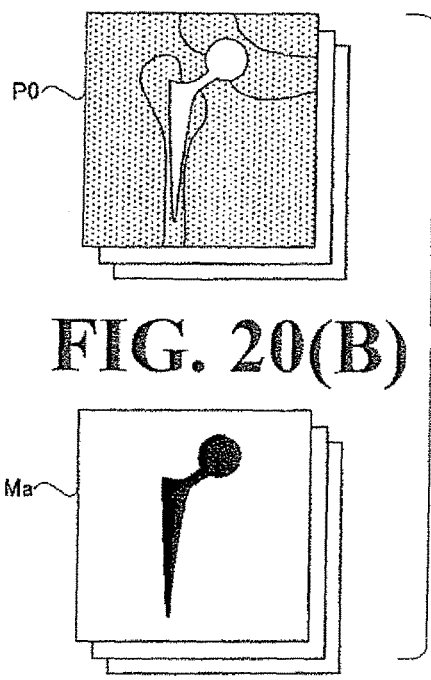
FIG. 20(B)
FIG. 20(C)
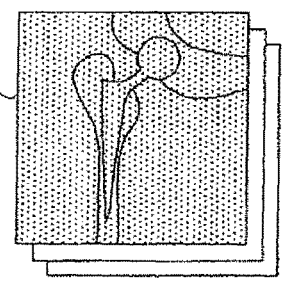
Metal Piece
Cancel
Processing

FIG. 22(A)
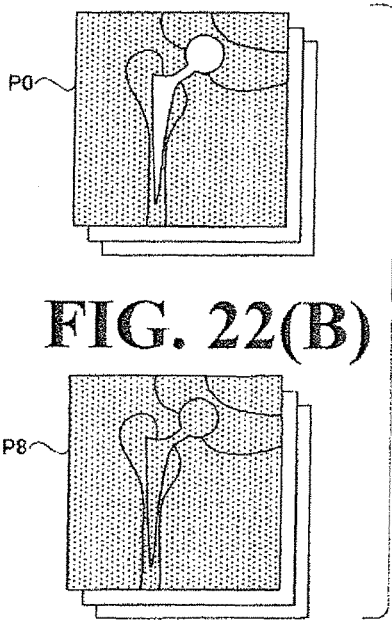
FIG. 22(B)
FIG. 22(C)
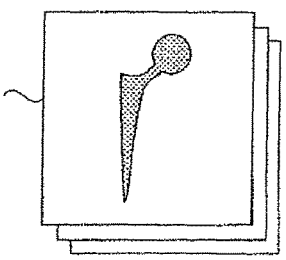
Metal Piece
Trimming
Processing

IMAGE PROCESSING DEVICE

CROSS REFERENCE TO RELATED APPLICATIONS

This application refers to and claims priority as a national-phase of PCT/JP2013/003016 filed May 10, 2013 the entire contents of which are incorporated herein by reference.

FIGURE SELECTED FOR PUBLICATION

FIG. 1

BACKGROUND OF THE INVENTION

Field of the Invention

The present invention relates to an image processing device to improve visual recognition of a radiation image, and particularly relates to the image processing device that can provide an image having high visual recognition despite incorporating an image of a metal piece into the radiation image.*

Technical Background

A medical facility equips the radiation device to obtain the subject's image using radiation. Such radiographic device comprises the image processing device to display an image having high visual recognition on the monitor by the addition of an image processing on the original image.

Some of the image processing devices can generate a tomographic image. According to such image processing device, when a plurality of original images that are continuously taken while changing the imaging direction are input, the original images are superimposed so as to output the tomographic image. A tomographic image is an image incorporating the image appearing when the subject is cross-sectionally imaged at a plan thereof.

Meantime, in the case of the subject who took a surgery to build up the bone with a metal piece in the past, an image of the metal piece is incorporated into the imaged original image. When the subject having the implanted metal piece inside body is imaged, the hardly radiation-transmissive metal piece is obviously incorporated into the original image. The metal piece on the original image appears as an extremely bright image on the original image.

The image processing device cannot generate the tomographic image having superior visual recognition by just simply superimposing the images incorporating the metal piece. Because a false image in the periphery of the metal piece incorporated into the generated tomographic image takes place. Then, according to the conventional image processing device, the tomographic image is generated by performing a separate image processing on the metal piece of the original image and other regions so as to prevent an occurrence of the false image in the tomographic image (e.g., see Patent Document 1, the entire contents of which are incorporated herein by reference).

A map capable of showing distribution of the metal piece in the original image is required so as to execute an image processing capable of reducing such false image. According to the conventional constitution, such map can be generated by executing a binarization processing on the original image. Provided the binarization processing is executed on the original image, an image as if in which an extremely dark metal piece incorporated into the original image is extracted can be obtained. The Otsu method can be applied to determine the threshold value relative to the binarization processing.

PRIOR ART DOCUMENTS

Patent Document 1: PCT/JP2012/003525
Non-Patent Document: Otsu N; A Threshold selection methods. IEEE from gray level histogram Trans. Systems Man, and Cybernetics 9: 62-66, 1979

ASPECTS AND SUMMARY OF INVENTION

Problems to be Solved by the Invention

However, there are following problems in the conventional constitution. Specifically, the binarization processing having the conventional constitution provides an inaccurate assignment of the metal piece.

According to the binarization processing relative to a conventional method, the metal piece cannot be extracted accurately. In some cases, more radiation absorptive cement is in-place in the periphery of the metal piece of the subject so that discrimination of the cement and the metal piece incorporated into the original image may be difficult when the binarization processing is performed. Accordingly, the conventional method for the binarization processing will include non-metal piece region in the metal piece region when the metal piece is extracted from the original image. This causes an erroneous recognition of the metal piece on the original image so that the tomographic image generation processing executed on the original image can be adversely impacted.

In addition, some original images have incorporated a fine whity component in the region other than the metal piece. In some cases, the binarization processing to extract the whity metal piece incorporated in the same original image may extract the fine component as well. Such erroneous extraction also provides an adverse impact on the generation processing of the tomographic image.

Under such circumstance, the present invention is completed and the purpose thereof is to provide an image processing device that can assuredly improve the visual recognition relative to a region other than a metal piece incorporated into the image by accurately discriminating the metal piece and other region's image relative to the image incorporating the metal piece. Means for solving the problem The present invention comprises the following system to solve the above problem. Specifically, the image processing device of the present invention that is an image processing device that executes an image processing on an original image P0 incorporating a metal piece obtained by radiation imaging of the subject having an implanted metal piece inside comprises; an image difference image generation means that is repeatedly operative to calculate the standard deviation of the pixel value of the attention pixel of the original image and the periphery of the attention pixel, an image calculation means that generates an calculation image by addition of the original image and the standard deviation image or subtraction of the standard deviation image from the original image, a calculation image binarization means that generates the binarization calculation image relative to the original image, a graph cut processing means that comprehends the distribution of the metal piece on the original image based on the binarization calculation image, obtains the representative value of pixel values of the region other than the metal piece of the original image and generates a map showing the distribution of the metal piece relative to the original image by executing the graph cut processing on the original image referring to each representative value.

Action and Effect

According to the composition of the present invention, the metal piece incorporated into the original image can be assuredly extracted based on the composition. That is, the standard deviation processing device that generates the standard deviation image in which the standard deviation is mapped relative to pixels constituting the image processing image of the present invention generates the standard deviation image in which the standard deviation is mapped relative to pixels constitution the original image, and then generates the calculation image by addition of the original image and the standard deviation image or subtraction of the standard deviation image from the original image, and further extracts the metal piece by the binarizing the calculation image thereof. In the certain calculation image, an image of the structure appearing in the region other than the metal piece of the original image is erased. Accordingly, the structure other than e.g. the metal piece incorporated whity on the original image will not appear in the calculation image. Accordingly, if the binarization processing capable of extracting e.g. the metal piece incorporated whity in the calculation image is added, an accurate graph cut processing can be performed so that an image originated in the structure other than the metal piece in the result image will never appear.

Further, the above image processing device preferably comprises; a metal piece cancel processing that generates a metal piece cancel image by canceling the metal piece incorporated into said original image from said original image referring to the extraction image, further wherein the metal piece is extracted from each original image continuously imaged while changing the imaging direction relative to the subject, a metal piece cancel tomographic image generation processing that generates metal piece cancel tomographic image by superimposing a plurality of the metal piece cancel image, a metal piece trimming processing that generates a trimming image by taking out the corresponding regions to the metal piece from the each original image referring to the extraction image, a metal piece tomographic image generation processing that generates metal piece tomographic image by superimposing a plurality of the trimming images, and a tomographic image generation means that executes the tomographic image adding processing so as to generate the synthetic tomographic image by adding the metal piece cancel tomographic image and the metal piece tomographic image.

Action and Effect

The image processing device of the present invention can be used for the case of generation of the tomographic image without occurrence of a false image in the periphery of the metal piece.

Further, the image processing device of the present invention may be mounted to a tomographic imaging device.

Effects of the Invention

The image processing device of the present invention generates the calculation image by addition or by subtraction relative to the original image and the standard deviation image in which the standard deviation is mapped relative to pixels constitution the original image. In the certain calculation image, an image of the structure appearing in the region other than the metal piece of the original image is erased. Accordingly, the structure other than e.g. the metal piece incorporated whity on the original image will not appear in the calculation image. Accordingly, if the binarization processing capable of extracting e.g. the metal piece incorporated whity in the calculation image is added, an accurate graph cut processing can be performed so that an image originated in the structure other than the metal piece in the result image will never appear.

BRIEF DESCRIPTION OF THE DRAWINGS

FIGS. 7(A),(B),(C) are schematic diagrams illustrating an operation of the image processing device of Embodiment 1.

FIGS. 20(A),(B),(C) are schematic diagrams illustrating an operation of the tomographic image generation element of Embodiment 1.

FIGS. 22(A),(B),(C) are schematic diagrams illustrating an operation of the tomographic image generation element of Embodiment 1.

DETAILED DESCRIPTION OF PREFERRED EMBODIMENTS

The image processing device of the present invention is an image processing device that executes an image processing on an original image P0 incorporating a metal piece obtained by radiation imaging of the subject having an implanted metal piece inside. Hereafter, the inventor illustrates the best modes of Embodiment of the present invention.

Embodiment 1

Figure 1:
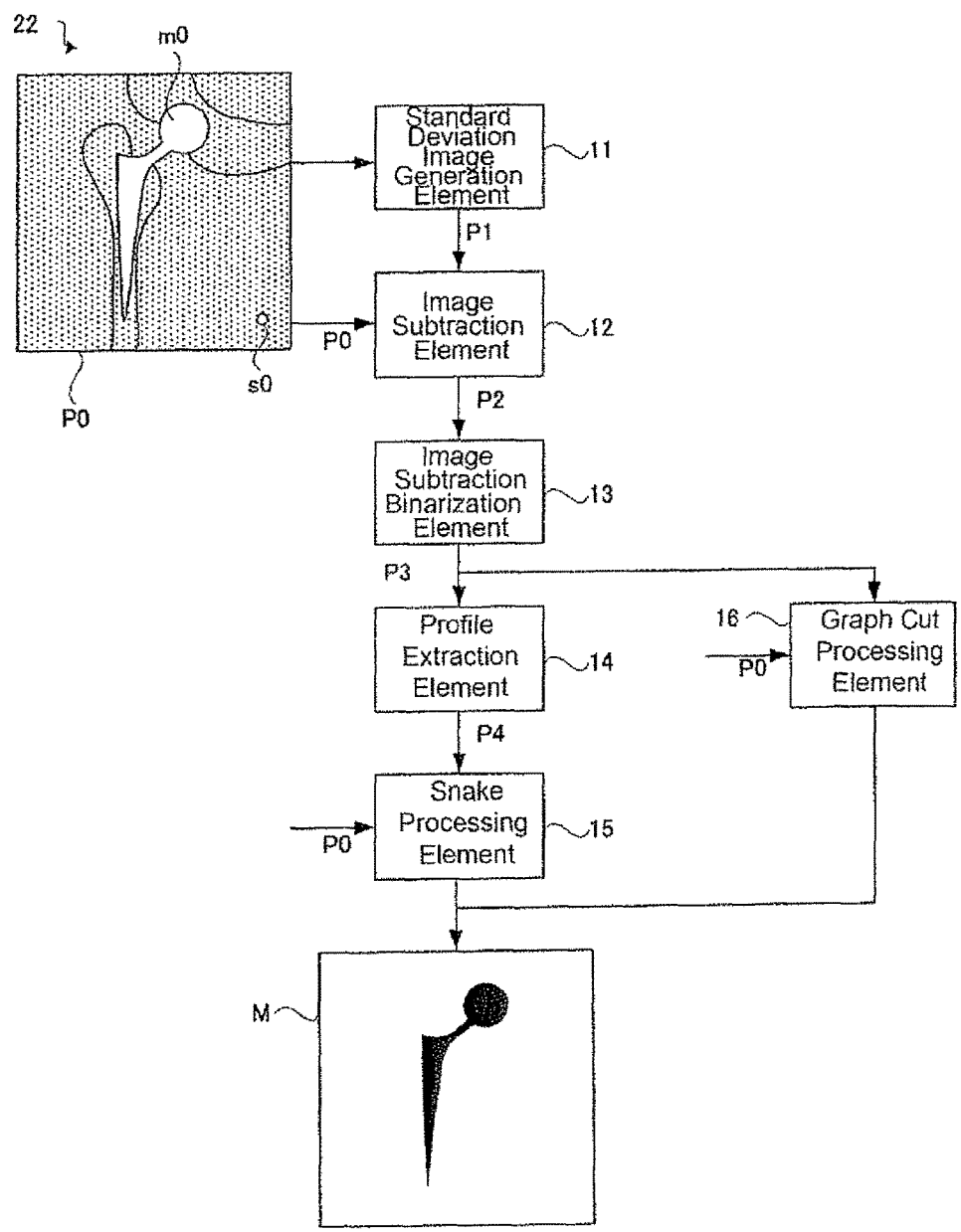
FIG. 1 is a functional block diagram illustrating the system of the image processing device of Embodiment 1.

First, the inventor sets forth Embodiment of the image processing device 22. Referring to FIG. 1, the system of the image processing device of the present invention outputs the map Ma showing the distribution of the metal piece incorporated into the original image P0 when the original image P0 is input. The original image P0 can be a variety of images, but it is given that the original image P0 is the image obtained by the X-ray radiography of the subject having an implant metal piece for the purpose of representing most effectively the characteristics of the present invention. And it is given that an image of the metal piece inside the subject is incorporated into the original image P0. Specifically, the original image P0 in FIG. 1 illustrates the metal piece m0 constituting an artificial joint.

The image processing device 22 comprises each element 11, 12, 12, 13, 14, 15, 16 in order to generate the map Ma based on the original image P0. The standard deviation image generation element 11 generates the standard deviation image P1 by executing the standard deviation filter on the original image P0. The image subtraction element 12 generates the subtraction image P2 by subtracting the standard deviation image P1 from the original image P0. The binarization element 13 generates the binarization subtraction image P3 by executing the binarization processing relative to the subtraction image P2. The profile extraction element 14 generates the profile extraction image P4 by extracting the profile of the binarization subtraction image P3. The snake processing element 15 recognizes the profile extracted in the profile extraction image P4 as the initial state and executes a segmentation processing by the snake relative to the original image P0 so as to generate the map Ma showing the distribution of the metal piece m0 relative to the original image. The graph cut processing element 16 generates the map Ma showing the distribution of the metal piece m0 relative to the original image based on the original image and the binarization subtraction image P3. The relationship between the operation in which the profile extraction element 14 and the snake processing element 15 are co-operative and the operation by the graph cut processing element is parallel. Relative the binarization subtraction image P3, the map Ma may be obtained by adding the image processing as to the snake processing or may be obtained by adding the image processing as to the graph cut processing.

The above standard deviation image generation element 11 corresponds to the standard deviation image generation means of the present invention and the image subtraction element 12 corresponds to the image calculation means of the present invention. Further, the above binarization element 13 corresponds to the binarization means of the present invention and the profile extraction element 14 corresponds to the profile extraction means of the present invention. Further, the snake processing element 15 corresponds to the snake processing means of the present invention and the graph cut processing element 16 corresponds to the graph cut processing means of the present invention. Further, the above subtraction image P2 corresponds to the calculation image of the present invention.

Figure 2:
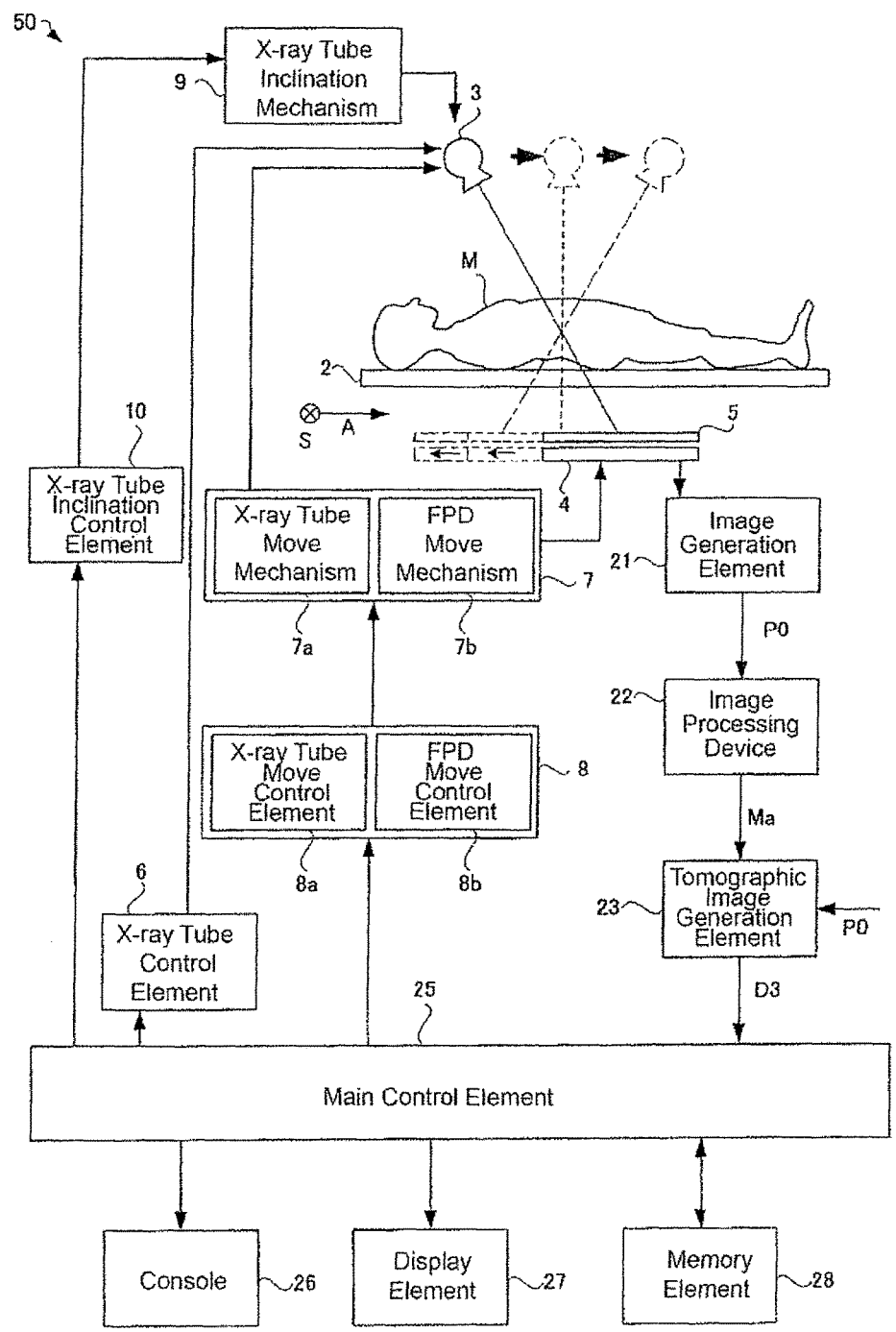
FIG. 2 is a functional block diagram illustrating the system of the imaging device of the original image of Embodiment 1.

A specific original image P0 input into the image processing device 22 is a series of the X-ray images imaged by the tomosynthesis device. The image processing device 22 of the present invention is the device that can make the tomographic image clear which is generated by the tomosynthesis device. Here, the tomographic image that is incorporating an image obtained when the subject is sliced at a cross section is generated by using a radiographic device. FIG. 2 is specifically illustrating such device. Referring to FIG. 2, the image processing device 22 comprises each element 11, 12, 13, 14, 15, 16 of FIG. 1.

The inventor sets forth Embodiment of the radiation tomographic device operable to generate a tomographic image of Embodiment 1. Further, X-ray of Embodiment is the radiation of the components of the present invention. Further, FPD (Flat Panel Detector) stands for Flat Panel X-ray Detector. The X-ray imaging device 50 of the present invention is for observation of artificial joint replacement surgery during the prognosis thereafter.

FIG. 2 is a functional block diagram illustrating the system of the X-ray imaging device 50 of Embodiment 1. Referring to FIG. 2, an X-ray imaging device 50 of Embodiment 1 comprises; a table 2 on which the subject M subjected to X-ray tomography is loaded, an X-ray tube 3 that is installed upper side of the table 2 (the first surface of the table 2) and radiates corn-like X-ray beam toward the subject M, a FPD 4 that is installed lower side of the table 2 (ground side of the table 2) and detects X-ray transmitting through the subject M, a synchronization move mechanism 7 that allows the X-ray tube 3 and the FPD 4 to make a synchronization move in the opposite direction each other while sandwiching the target region of the subject M under the condition in which the center axis of the cone-like X-ray beam always coincides with the center of the FPD 4, a synchronization move control element 8 that controls the synchronization move mechanism 7, and an X-ray grid 5 that absorbs the scattered X-ray set as covering the X-ray detection surface of the FPD 4 to detect X-ray. In this mode, the table 2 is in-place in the position sandwiched by the X-ray tube 3 and the FPD 4.

The synchronization move mechanism 7 comprises the X-ray tube move mechanism 7a that moves the X-ray tube in the body axis direction A relative to the subject M and the FPD move mechanism 7b that moves the FPD 4 in the body axis direction A relative to the subject M. Further, the synchronization move control element 8 comprises the X-ray tube move control element 8a that controls the X-ray tube move mechanism 7a and the FPD move control element 8b that controls the FPD move mechanism 7b. When the original image P0 is continuously imaged, the synchronization move control element 8 moves the X-ray tube and the FPD 4 in the opposite direction each other.

The X-ray tube 3 radiates structure-wise cone-like pulse X-ray beam to the subject M repeatedly in accordance with control by the X-ray tube control element 6. The collimater is attached to the X-ray tube 3 to collimate the X-ray beam to cone shape like a pyramid. And the X-ray tube 3 and the FPD 4 form the imaging system 3, 4 that images the X-ray projection image. The X-ray control element 6 controls the X-ray tube 3 according to the predetermined values specifying tube electric current, tube electric voltage and pulse width therefor and so forth.

The synchronization move mechanism 7 comprises a step of moving the X-ray tube and the FPD 4 in synchronization relative to the subject M. The synchronization move mechanism 7 moves straight the X-ray tube 3 along the straight line trajectory (longitudinal direction of the table 2) parallel to the body axis direction A of the subject M in accordance with control by the synchronization move control element 8. The move directions of the X-ray tube 3 and the FPD 4 coincide with the longitudinal direction of the table 2. In addition, during the examination, the cone-like X-ray beam radiated from the X-ray tube 3 is always radiated toward the target region of the subject M and the X-ray radiation angle thereof e.g. can be changed from the initial angle −20° till the final angle 20° by changing angle of the X-ray tube 3. Such change of X-ray radiation angle can be conducted by the X-ray tube inclination mechanism 9. The X-ray tube inclination control element 10 is installed so as to control the X-ray tube inclination mechanism 9.

And the X-ray imaging device 50 of Embodiment 1 further comprises a main control element 25 that controls comprehensively each control element 6, 8, 10, 11, 12 and a display 27 that displays a tomographic image. The main control element 25 comprises a CPU and brings each control element 6, 8, 10 and each element 21, 22, 23, set forth later, into reality by executing a variety of programs. The memory element 28 stores all data related to control of the X-ray imaging device, e.g. parameters related to the control of the X-ray tube 3. The console 26 is used to input each operation relative to the X-ray imaging device 50 by the operator.

Further, the synchronization move mechanism 7 moves straight the FPD 4 installed under side of the table 2 in the straight line of the body axis direction A (longitudinal direction of the table 2) in synchronization of straight move of the X-ray tube 3 as set forth above. And the move direction is opposite direction to the move direction of the X-ray tube 3. Specifically, the cone-like X-ray beam in changing the position of the focal point of the X-ray tube 3 and the radiation direction along with move of the X-ray tube 3 are structure-wise always received with all surfaces of the detection surface of the FPD4. Accordingly, the FPD 4 can receive e.g. 74 projection images while moving in the opposite direction relative to the X-ray tube 3 each other in synchronization during one examination. Specifically, referring to FIG. 2, the imaging systems 3, 4 move from the initial position illustrated as a solid line to the position illustrated as a dashed-line via the position illustrated as a broken line facing each other. Specifically, a plurality of X-ray projection images are taken while changing the positions of X-ray tube 3 and the FPD 4. By the way, the cone-like X-ray beam always are received by all surfaces of the detection surface of the FPD 4 so that the center axis of the cone-like X-ray beam during imaging always coincides with the center point of the FPD 4. Further, the center of the FPD 4 moves straight and such move is in the opposite direction relative to the move of the X-ray tube 3. That is, it will be understood that the system moves the X-ray tube 3 and the FPD 4 in synchronization and in the opposite direction each other along the body axis direction A.

Principal of Acquisition of a Tomographic Image

Figure 3:
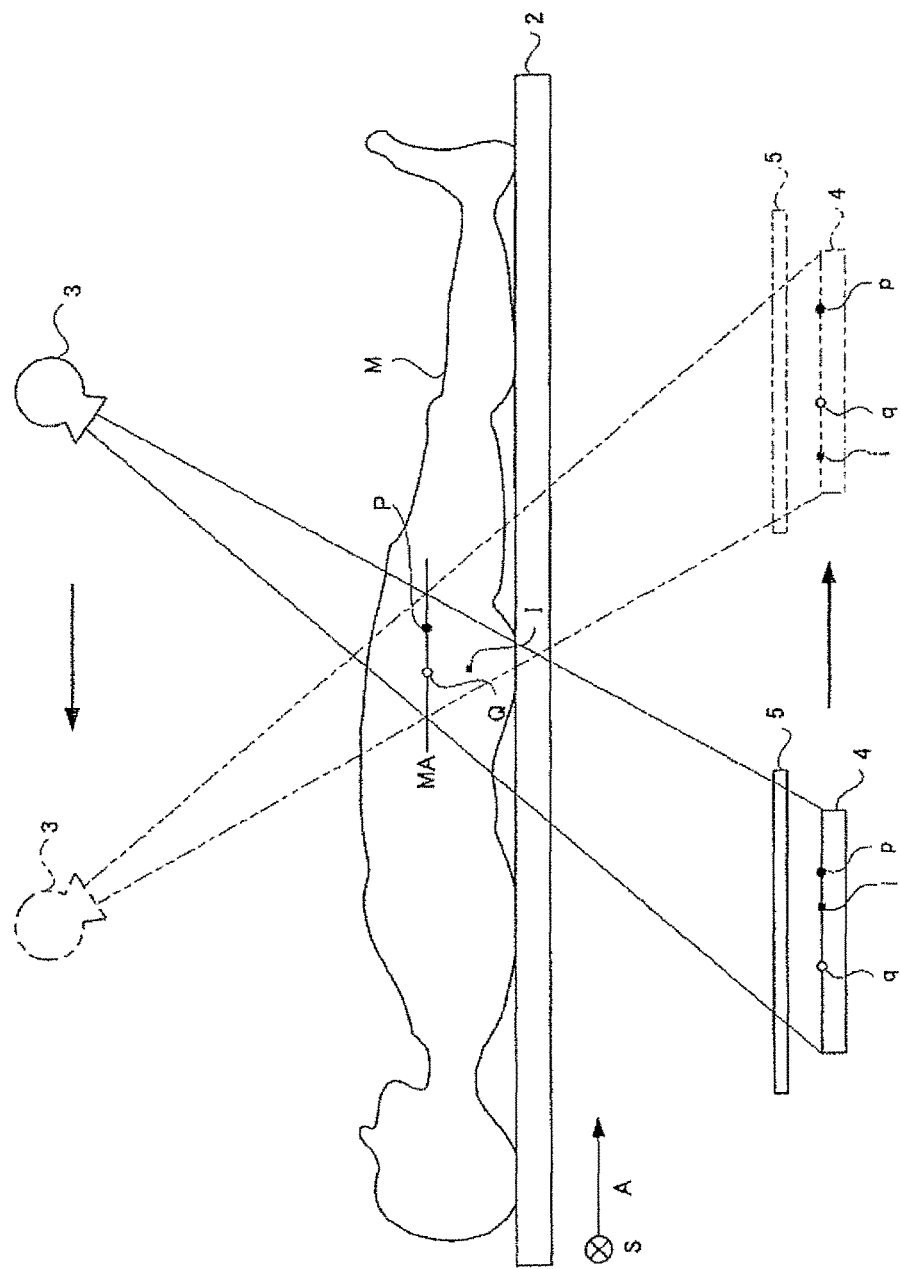
FIG. 3 is a schematic diagram illustrating an acquisition principle of the tomographic image of Embodiment 1.

Next, the inventor sets forth the principal of acquisition of a tomographic image of Embodiment 1. According to the system of Embodiment 1, the tomographic image can be generated by generating a plurality of the tomographic images that are images taken when the subject M is sliced on the plan. FIG. 3 is a schematic diagram illustrating the acquisition method for the tomographic images taken by the X-ray imaging device of Embodiment 1. For example, referring to FIG. 3, as the virtual plan (the base slice section MA) parallel to the table 2 (horizontal relative to the perpendicular) is set forth, a series of the original images P0 is generated by the image generation element 21 while the FPD 4 moves in synchronization in the opposite direction relative to the X-ray tube 3 according to the radiation direction of the cone-like X-ray beam from the X-ray tube 3 so that the points p, q in-place on the base slice section can be always projected to the fixed-points p, q on the X-ray detection surface of the FPD 4. The projection images of the subject M are incorporated into the series of the original images P0 while changing the position thereof. Then, providing the series of original images P01 is reconstructed by the tomographic image generation element 23, the images (e.g. fixed point p, q) in-place on the base slice section MA are accumulated and the X-ray tomographic image can be imaged. On the other hand, the point I in-place out of the base slice section MA is incorporated into the series of images of the subject M as a point i while changing the projection position on the FPD 4. The point i, differently from the fixed points p, q, will not focus into an image and will be out of focus at the step of superimposing the X-ray projection images by the tomographic image generation element 23. Accordingly, the series of projection images are superimposed so that the X-ray tomographic image incorporating only the image in-place on the base slice section MA of the subject M can be obtained. Accordingly, the projection images are simply superimposed so that the tomographic image on the base slice section MA can be obtained. The tomographic image generation element 23 corresponds to the tomographic image generation means of the present invention. The tomographic image generation element 23 corresponds to the tomographic image generation means of the present invention.

Further, the tomographic image generation element 23 can obtain the same tomographic image at any slice section horizontal to the base slice section MA. During imaging, the projection position of the point i relative to the FPD 4 moves but the move rate increases according to increasing distance between the point I before projection and the base slice surface MA. Based on this fact, if the obtained series of images of the subject M should be reconstructed while shifting to the body axis direction A at the predetermined pitch, the tomographic image at the slice section parallel to the base slice section MA can be obtained. Such reconstruction of a series of tomographic images can be executed by the tomographic image generation element 23.

Operation of the Image Processing Device 22: Operation of the Standard Deviation Image Generation Element 11

Figure 4A:
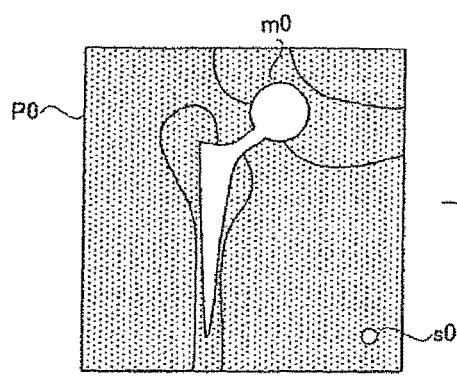
FIGS. 4(A),(B) are schematic diagrams illustrating an operation of the image processing device of Embodiment 1.

Next, the operation of the image processing device 22 is specifically set forth. Given the original image P0 incorporating the metal piece m0 is input to the image processing device 22, the original image P0 is input to the standard deviation image generation element 11 and then the standard deviation image P1 is generated as illustrated in FIGS. 4(A),(B). The standard deviation image P1 is the image in which the standard deviation relative to pixels constituting the original image P0 is mapped. The standard deviation is the measure of the dispersion used in statistics and specifically, the measure of the dispersion of pixel values of certain pixels constituting the original image and pixels in the periphery of pixels thereof.

Figure 5:
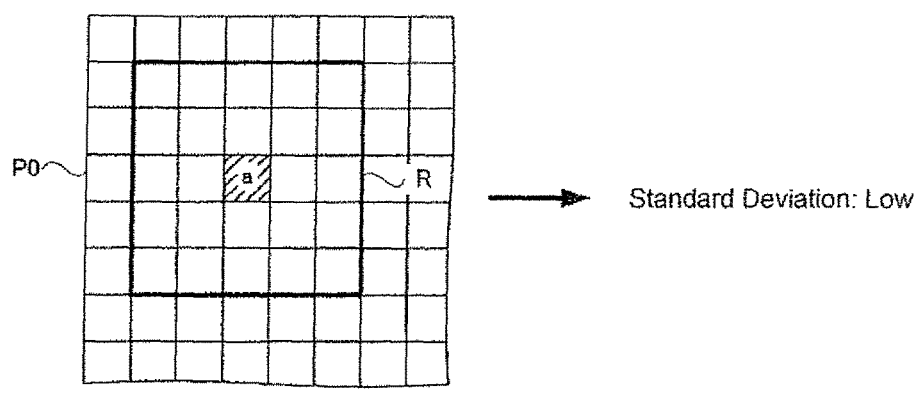
FIG. 5 is a schematic diagram illustrating an operation of the image processing device of Embodiment 1.

The operation of the standard deviation image generation element 11 is set forth so as to generate the standard deviation image P1. Referring to FIG. 5, the standard deviation image generation element 11 specifies one of pixels constituting the original image P0 as an attention pixel a. And the standard deviation image generation element 11 specifies e.g., a square region of 11 length by 11 width, having the attention pixel in the center thereof, as the attention region R. The attention region R should include the attention pixel a. The standard deviation image generation element 11 calculates these standard deviations by obtaining pixel values included in the attention region R from the original image P0. The certain calculated standard deviation is the value relative to the attention pixel a. In addition, for the convenience of drawing, the attention region R in FIG. 5 is the square of 5 length by 5 width.

The standard deviation image generation element 11 specifies all pixels constituting the original image P0 as the attention pixel a in order and calculates the standard deviation value every attention pixel a. Once the standard deviation image generation element 11 calculates the standard deviation values of all pixels constituting the original image P0, it conducts the mapping of standard deviation values. Specifically, the standard deviation image generation element 11 repeats the operation by which the standard deviation values are set in-place in the position of the attention pixel a upon calculation. Accordingly, all calculated standard deviation values are set in-place in one image. The calculated standard deviation values are pixel values in the standard deviation image P1 obtained in such mode. The series of operations conducted by the standard deviation image generation element 11 can generate and present the standard deviation image P1 by activating the standard deviation filter that specifies the calculation method for the attention region R and the standard deviation relative to each pixel constituting the original image P0.

The meaning of the standard deviation image P1 generated in such mode is set forth. Referring to FIG. 5, the state when the standard deviation image generation element 11 set up a certain attention pixel a on the original image P0 and the attention region R is illustrated. In this state, pixels having the similar pixel value exist in the periphery of the attention pixel a. The standard deviation of the attention pixel a tends to be a small value.

Figure 6:
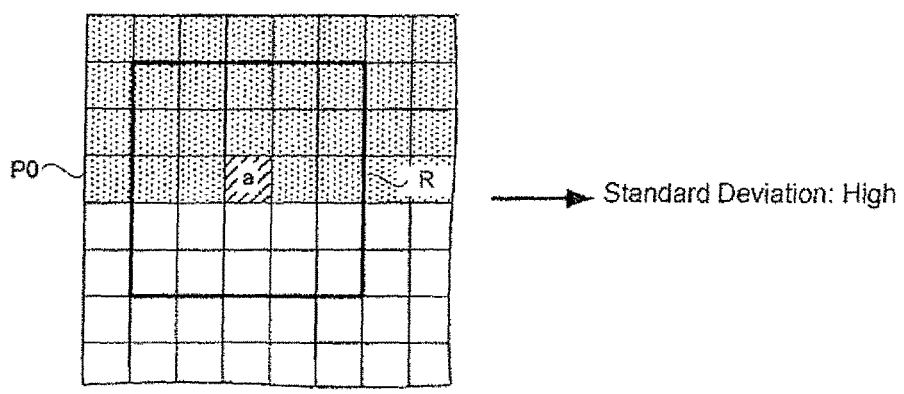
FIG. 6 is a schematic diagram illustrating an operation of the image processing device of Embodiment 1.

Also referring to FIG. 6, the state when the standard deviation image generation element 11 set up a certain attention pixel a on the original image P0 and the attention region R is illustrated. The attention pixel a at this state is given as the position thereof is in the border between the metal piece m0 and the other region relative to the original image P0. At this time, pixel values of the attention pixel a and the surrounding pixels thereof are dispersed. The standard deviation of the attention pixel a tends to be a high value.

Figure 4B:
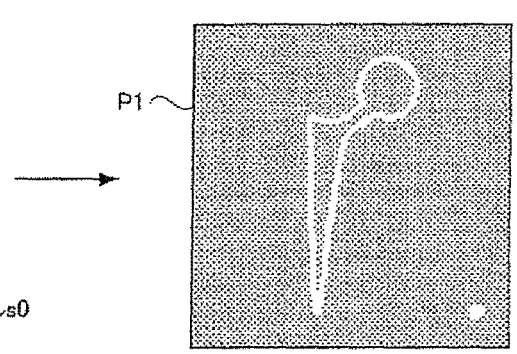

Specifically, the region having a high pixel value corresponds to the region where pixel values relative to the original image P0 are dispersed and the region having a small pixel value corresponds to the region where pixel values relative to the original image P0 are similar. As the matter of fact, the standard deviation image P1 provides the image in which the boundary region between the metal piece m0 and the other region on the original image P0 shows up as the high pixel value (referring to FIG. 4(B)).

Further, a bright spot s0 is incorporated into the original image. The bright spot s0 is obviously not belonging to the metal piece m0 but it shows up brightly as well as the metal piece m0 on the original image P0. The spot s0 is a result in which the material other than the metal piece relative to the subject M, through which X-ray hardly transmits. The spot s0 will be likely extracted together when the metal piece m0 is being extracted from the original image P0. This kind of phenomenon should be prevented from an exact extraction standpoint as to the metal piece.

The inventor sets forth how the spot s0 appears on the standard deviation image P1. The region corresponding to the spot s0 on the standard deviation image P1 shows up as a high pixel value as well as the metal piece m0. Because, the standard deviation value of pixels constituting the spot s0 is high. The spot s0 is the pixel showing up relative to the original image P0. Accordingly, the pixel constituting the spot s0 is bright and relatively dark pixels are distributed in the surrounding region thereof. Accordingly, when the calculation of the standard deviation as to the spot s0 is conducted, the high standard deviation value can be obtained because of the state as set forth referring to FIG. 6.

Operation of the Image Processing Device 22: Operation of the Image Subtraction Element 12

The generated standard deviation image P1 is input to the image subtraction element 12. Referring to FIGS. 7(A),(B), and (C), the image subtraction element 12 generates the subtraction image P2 by subtracting the standard deviation image P1 from the original image P0.

The inventor sets forth what the subtraction image P2 is. Referring to FIG. 7(C), the subtraction image P2 is incorporating the image as if darkly surrounding the bright metal piece m0. The inventor sets forth the rationale by which the subtraction image P2 is in such mode. It is considered that when the standard deviation image P1 is subtracted from the original image P0, how much the subtraction level is different from region to region of the original image. The high pixel value region and the low pixel value region are mixed in the original image P1 so that the subtraction level for the original image may vary depending on the region of the image. The pixel of the original image P0 corresponding to the region having the high pixel value relative to the standard deviation image P1 will largely loose the pixel value thereof by the subtraction processing and the pixel of the original image P0 corresponding to the region having the high pixel value relative to the standard deviation image P1 will much less loose the pixel value thereof by the subtraction processing.

As set forth above, the region having the high pixel value relative to the standard deviation image P1 is the boundary between the metal piece m0 relative to the original image P0 and the other region. Accordingly, when the subtraction processing is executed on the original image P0, the pixel value of the pixel in-place in the boundary region largely decreases so that the image of FIG. 7(B) may be provided. The subtraction image P2 is the image as if of which the ambiguous pixels whether they are belonging to the metal piece in-place in the profile of the metal piece m0 on the original image P0 or not are painted with the dark pixel.

Next, it is considered that the bright spot s0 in-place in the region other than the metal piece on the original image P0 is how appears by the subtraction processing. A high pixel value is assigned to the corresponding region to the spot s0 relative to the standard deviation image P1. Accordingly, when the standard deviation image P1 is subtracted from the original image P0, the pixel value of the pixel constituting the spot s0 will largely decrease. Accordingly, the image of the component appearing as the bright spot p0 in the region other than the metal piece of the original image P0 is erased and will not show up on the subtraction image P2.

[Operation of the Image Processing Device 22: Operation of the Binarization Element 13]

Figure 8:
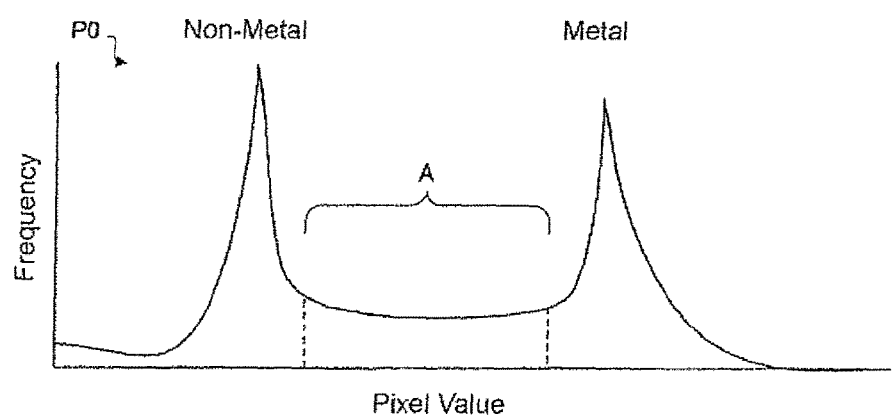
FIG. 8 is a schematic diagram illustrating an operation of the image processing device of Embodiment 1.

The subtraction image P2 is output to the binarization element 13 and the subtraction image P2 is executed by the binarization processing. The inventor sets forth that the right region of the metal piece m0 relative to the original image P0 can be extracted by this mode. FIG. 8 is a histogram, wherein the original image P0 is developed by the pixel value. Two peaks including a peak derived from the metal piece m0 and another peak derived from the region other than the metal piece appear in the original image P0. It is considered that the case in which the metal piece m0 is being extracted from the original image P0. In this case, it seems better that the threshold between two peaks is set so that it can be found whether the pixel belongs to the metal piece m0 or not on the basis of that whether the pixel value of the pixel constituting the original image P0 is higher than the threshold value or not.

However, the pixels having intermediate value shown as the reference A are distributed between two peaks. Such pixels exist more in the boundary between the metal piece m0 and the region other than that on the original image P0. If the threshold processing is conducted on the ambiguous region whether a metal or not, the judgment might be wrong. Specifically, the pixel even not belonging to the metal piece m0 relative to the original image P0 may be judged to be assigned to the metal piece m0 or despite the pixel actually belonging to the metal piece m0, it may be judged as not to be assigned to the metal piece m0. Further, the bright spot s0 appeared in the region other than the metal piece of the original image is belonging to the intermediate region shown as the reference A. When the original image is binarized, if the spot s0 has a brighter pixel value than the threshold value, the spot s0 may be wrongfully assigned to the metal piece.

Figure 9:
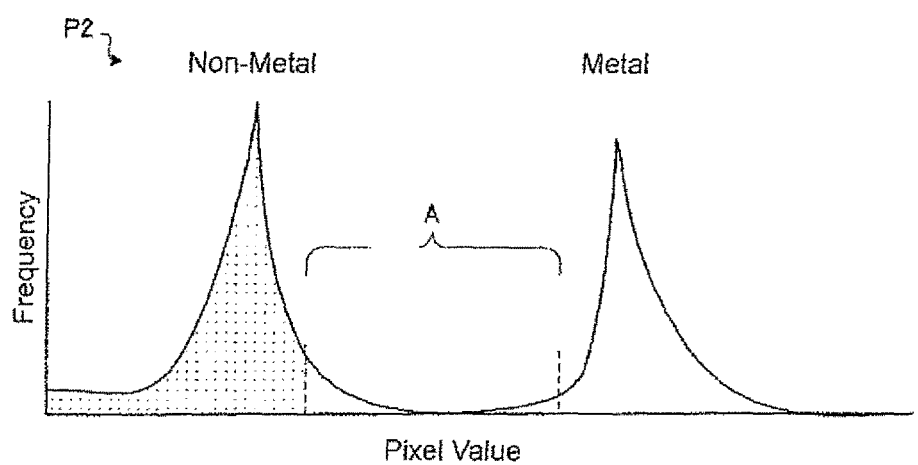
FIG. 9 is a schematic diagram illustrating an operation of the image processing device of Embodiment 1.

Accordingly, in the constitution of Embodiment 1, when the metal piece m0 is extracted, no threshold processing is directly executed on the original image P0. FIG. 9 is a histogram of the subtraction image P2. Comparing to FIG. 8, it is noticeable that a number of pixels in the region A decreased. Because all pixel values of the ambiguous pixels surrounding the metal piece m0 on the original image P0 whether belonging to the metal piece and not or the pixels constituting the spot s0 on the original image P0 largely decrease and are grouped into the shaded region other than the metal piece in FIG. 9.

Figure 10A:
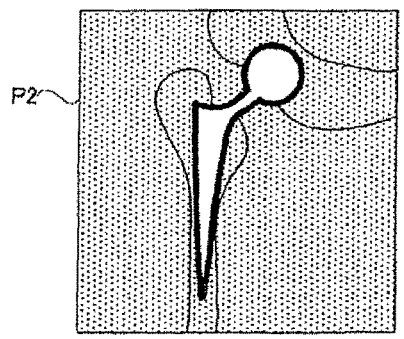
FIGS. 10(A),(B) are schematic diagrams illustrating an operation of the image processing device of Embodiment 1.
Figure 10B:
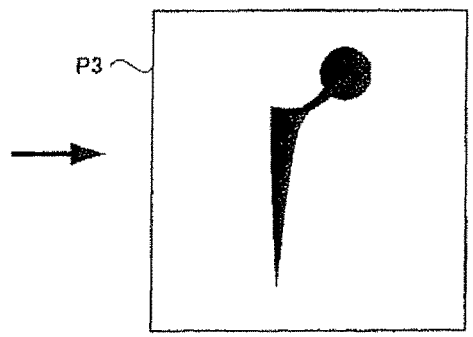

Referring to FIGS. 10(A), (B), the binarization element 13 generates the binarization subtraction image P3 showing two regions including the region that is surely belonging to the metal piece m0 relative to the original image P0 and the ambiguous region belonging to either the metal piece or the non-metal piece by executing the threshold processing on the subtraction image P2. At this time, given the pixel value of the metal piece m0 incorporated into the original image P0 is known in advance, the threshold value employed by the binarization element 13 may be decided based on the pixel value thereof or may be decided by using Otsu method. Further, the binarization subtraction image P3 corresponds to the binarization calculation image of the present invention.

Figure 11A:
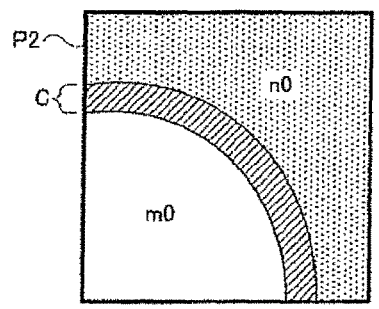
FIGS. 11(A),(B) are schematic diagrams illustrating an operation of the image processing device of Embodiment 1.
Figure 11B:
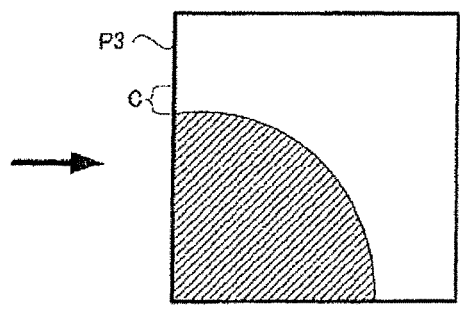

FIGS. 11(A), (B) is specifically illustrating the processing which the binarization element 13 executes on the subtraction image P2 by taking out a region of the subtraction image P2. In the subtraction image P2, the dark belt-like region C is mixed in between the bright region incorporating the metal piece m0 and the dark region represented by the reference n0 which is not the metal piece m0. The belt-like region C is the region that corresponds to the region in-place in the profile of the metal piece m0 incorporated into the original image P0 and of which the pixel value drastically decreased by the image subtraction processing. When the binarization processing is executed on the subtraction image in this mode, the belt-like region C will not be incorporated into the region indicating a metal. Accordingly, the binarization element 13 divides the original image P0 to the region that is surely belonging to the metal piece m0 and the ambiguous region belonging to either the metal piece or the non-metal piece.

Operation of the Image Processing Device 22: Confirmation of the Distribution of the Metal Piece m0 Incorporated into the Original Image P0

Accordingly, the generated binarization subtraction image P3 is the image in which the metal piece m0 is exactly taken out from the original image P0 compared with the image for which the original image P0 is simply binarized. However, there is a method that can perform further exactly the extraction of metal piece based on the binarization subtraction image P3.

Basically, the binarization subtraction image P3 is the image of which the ambiguous region whether the metal piece or non-metal piece is counted as the non-metal region so that the distribution of the metal piece on the original image P0 must be broader than the distribution of the binarization subtraction image P3. Therefore, the image processing device of Embodiment 1 executes the confirmation of the distribution of the metal piece m0 incorporated into the original image P0 using the binarization subtraction image P3 by the subsequent image processing. Such image processing includes two methods, whichever is capable of extracting exactly the metal piece m0 from the original image P0. Two methods include specifically the method utilizing the snake method and the graph cut method. The inventor sets forth two methods in order.

Operation of the Image Processing Device 22: Operation of the Snake Method

Figure 12A:
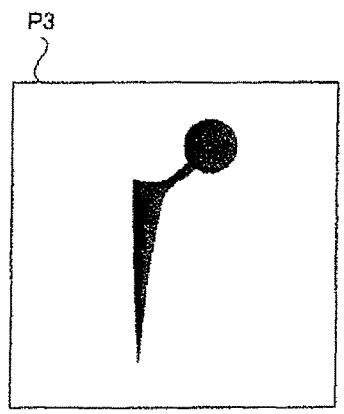
FIGS. 12(A),(B) are schematic diagrams illustrating an operation of the image processing device of Embodiment 1.
Figure 12B:
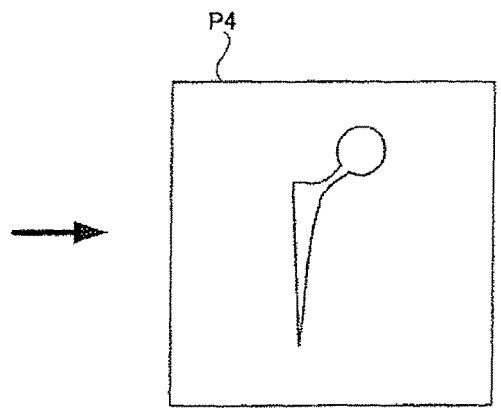
Figure 14A:
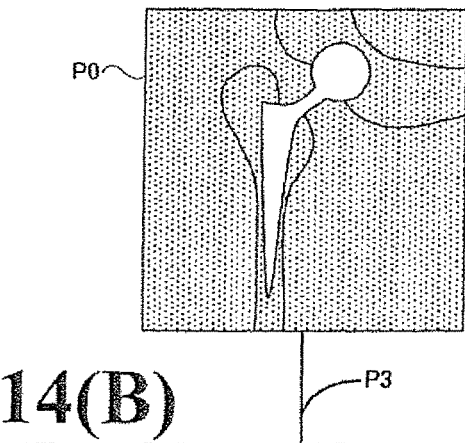
FIGS. 14(A) (B)(C) are schematic diagrams illustrating an operation of the image processing device of Embodiment 1.

First, the inventor sets forth the snake method. When this method is adopted, the binarization subtraction image P3 (FIGS. 12(A), (B)) will be first sent to the profile extraction element 14. Referring to FIGS. 14(A), (B), (C), the profile extraction element 14 generates the profile extraction image P4 by executing the profile extraction processing on the binarization subtraction image P3. The profile extraction image P4 is the image as if the silhouette of the metal region (the region assuredly belonging to the metal piece m0 of the original image P0) incorporated into the binarization subtraction image P3 is traced by a pen. According to the profile extraction processing, the metal region of the binarization subtraction image P3 appears on the profile extraction image P4 as the ring drawn by closing the line having a constant line width.

Figure 13A:
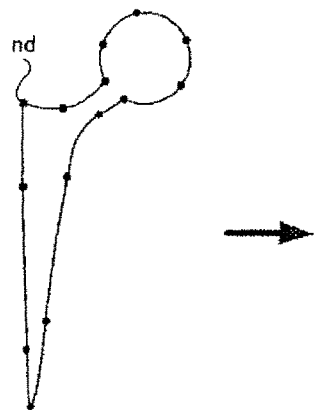
FIGS. 13(A) (B) are schematic diagrams illustrating an operation of the image processing device of Embodiment 1.
Figure 13B:
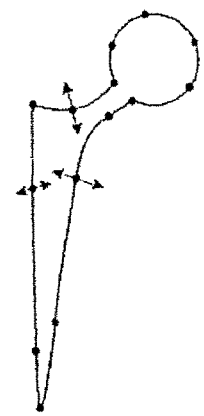

The profile extraction image P4 is sent to the snake processing element 15. The snake processing element 15 analyzes the mode of the circular figure on the profile extraction image P4 and then sets the node nd as a measure when the figure in FIG. 13(A) is deformed. Then, referring to FIG. 13(B), the snake processing element 15 decides the right profile of the metal piece m0 relative to the original image P0 while moving as if swinging the node nd. The snake processing element 15 is operative referring to the original image P0. The snake processing element 15 repeatedly reforms while applying a figure to the original image P0 and looks for the suitable figure mode from the difference of pixel values between the pixel value of the pixel included in the figure of the original image P0 and the pixel value of the non-included pixel while keeping the smooth mode. The snake processing element 15 recognizes the mode of the finally decided figure and binarizes so as to divide the inside region and the outside region of the figure. Then, referring to FIG. 1, the binarization image map Ma in which the metal piece m0 is suitably extracted from the original image P0 can be generated.

Operation of the Image Processing Device 22: Operation of the Graph Cut Method

Figure 14B:
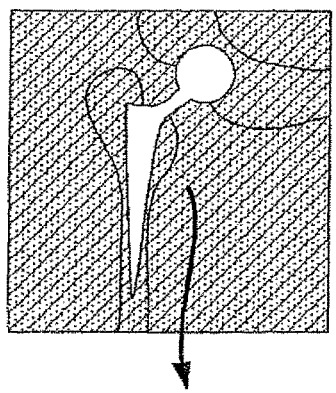
Figure 14C:
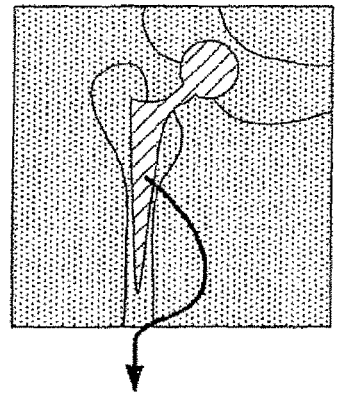
Figure 15:
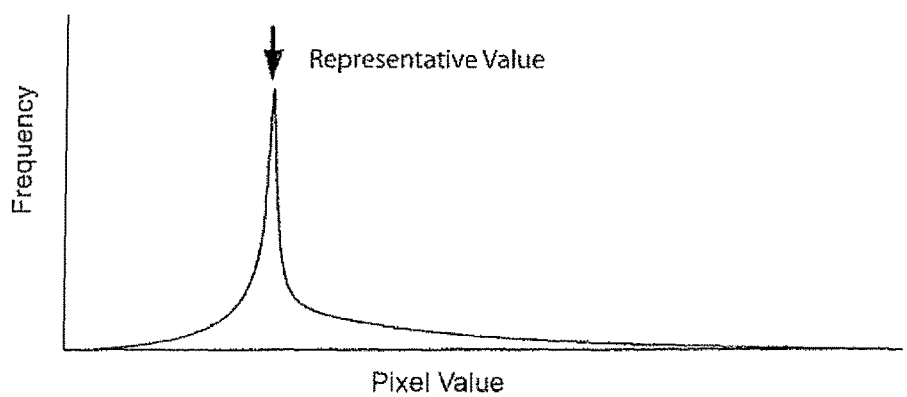
FIG. 15 is a schematic diagram illustrating an operation of the image processing device of Embodiment 1.

The image processing device can generate the map Ma by the different method from the above sanke method. Specifically, the image processing device 22 generates the map Ma by suitably extracting the metal piece m0 from the original image P0 based on the graph cut method. The binarization subtraction image P3 is the beginning of the processing even by the graph cut method, Given the graph cut method is adopted to generate the map Ma, the binarization subtraction image P3 is sent out to the graph cut processing element 16. Referring to FIGS. 14(A)-(C), the graph cut processing element 16 obtains the representative value obj of the pixel value of the region corresponding to the metal piece m0 relative to the original image P0 based on the binarization subtraction image P3. The representative value obj is the most general pixel value relative to the metal piece m0. The region assuredly belonging to the metal piece m0 relative to the original image P0 is first set referring to the binarization subtraction image P3 for the graph cut processing element 16 to calculate the representative value obj. Then, referring to FIG. 15, the graph cut processing element 16 performs the histogram analysis as to the certain region and obtains the pixel value most often appearing at the certain region. The pixel value obtained by this histogram is the representative value obj of the metal piece.

The graph cut processing element 16 obtains the representative value bg of the pixel value of the region corresponding to the region other than the metal piece m0 relative to the original image P0. The representative value bg is the most general pixel value relative to the region other than metal piece m0. The region assuredly belonging to the region other than the metal piece m0 relative to the original image P0 is first set referring to the binarization subtraction image P3 for the graph cut processing element 16 to calculate the representative value bg. Then, the graph cut processing element 16 performs the histogram analysis as to the certain region and obtains the pixel value most often appearing at the certain region. The pixel value obtained by this histogram is the representative value bg of the metal piece, Then, the region corresponding to the region other than the metal piece m0 in the binarization subtraction image P3 includes the ambiguous region whether belonging to the metal piece or not relative to the original image P0. Accordingly, when the representative value bg is decided, it seems that the obtained representative value bg may deviate from the pixel value most frequently appeared in the region other than the metal piece m0 by an impact of the pixel value of the ambiguous region. Assuredly, the histogram generated when the graph cut element 16 obtains the representative value bg includes the pixel of the ambiguous region.

However, the pixel value of the ambiguous region is basically similar to the pixel value of the metal piece and the pixel value of the ambiguous region, appearing in the histogram, is fewer compared to the pixels relative to the region other than the metal piece m0. Accordingly, the peak formed by the ambiguous pixels in the histogram is away from the main peak formed by the pixels of the region other than the metal piece m0 and lower than the main peak. The graph cut element 16 obtains the representative value bg referring to the top of the main peak so that the pixel of the ambiguous region whether the metal piece or not may not be involved for the decision of the representative value bg.

The graph cut element 16 performs the graph curt processing on the original image P0 based on the representative value obj and the representative value bg, and extracts exactly the distribution of the metal piece m0 incorporated into the original image P0. The graph cut processed pixels are exactly assigned whether the pixel thereof belongs to the metal piece or the non-metal region.

Figures 16A, 16B:
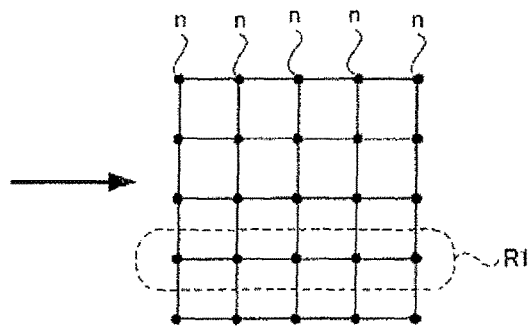
FIGS. 16(A),(B) are schematic diagrams illustrating an operation of the image processing device of Embodiment 1.

FIGS. 16(A),(B) are illustrating the mode of a node n used for the graph cut method. It is given that the image comprises the pixel two dimensionally arrayed as illustrated in FIG. 16(A). The graph cut method interprets as the pixel a is a node n connected each other. Each node corresponds to each pixel a. Accordingly, nodes n are two dimensionally arrayed. Each node n that is two dimensionally arrayed is connected to the adjacent node n each other. The connected node n each other is closely related each other and make a lump. Then, the lump uniformly made of the entirety of image is dissolved into two lumps by disconnecting each node n one by one. Consequently, one of dissolved two lumps only comprises the node n corresponding to the pixel belonging to the metal piece. The other lump comprises only the node n corresponding to the pixel belonging to non-metal region.

Figure 17A:
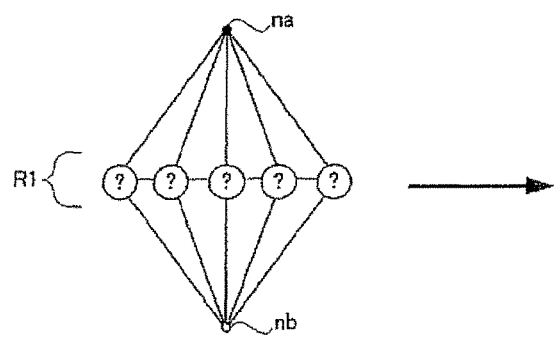
FIGS. 17(A),(B) are schematic diagrams illustrating an operation of the image processing device of Embodiment 1.
Figure 17B:
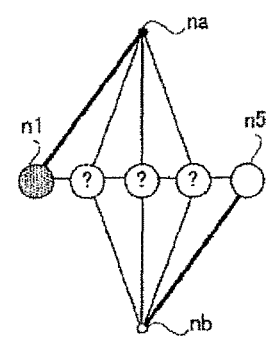

FIGS. 17 (A), (B) are illustrating the first steps of the graph cut method. For ease of explanation, the inventor extracts the line of node n having the reference R1 and sets forth. Firstly, two nodes na, nb are added in addition to the node n corresponding to the pixel a. The node na is a virtual node representing the pixel belonging to the metal piece. The node na is connected to all nodes n. The node nb is a virtual node representing the pixel belonging to the non-metal region. The node nb is also connected to all nodes n.

Next, the graph cut processing element 16 links the representative value obj to the node na and also links the representative value bg to the node nb. And next, the graph cut processing element 16 assigns the node n. For example, referring to FIGS. 17(A),(B), the graph cut processing element 16 connects the node na having the same pixel value as the representative value obj among the nodes n to the node na. Further, also the node n5 having the same pixel value as the representative value bg among the nodes n is connected to the node nb.

Figure 18A:
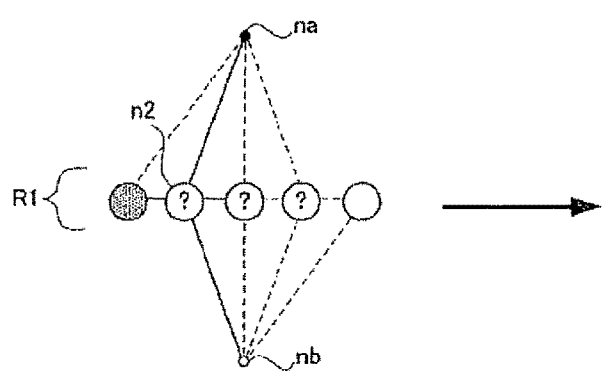
FIGS. 18(A),(B) are schematic diagrams illustrating an operation of the image processing device of Embodiment 1.
Figure 18B:
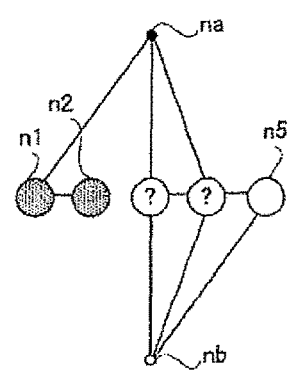

The node n2 illustrated in FIGS. 18 (A), (B) are the ambiguous pixel whether belonging to the metal piece or not. The graph cut processing element 16 notices the connection lines connected to the node n2 when assigning the node n2. An evaluation value called cost is assigned to these lines. The graph cut processing element 16 divides the connection lines by comparing the costs. The cost is decided based on the pixel value of the pixel corresponding to the node n. Specifically, in the case of adjacent pixels having an similar pixel value, the cost of the connection line between nodes n corresponding to adjacent pixels is set as low. Then, in the case of the pixel value of a pixel, which is a value representing less X-ray exposure, the cost of the connection line between node n and the node na corresponding to the instant pixel will be set as low. Also, in the case of the pixel value of a pixel, which is a value representing a large X-ray exposure, the cost of the connection line between node n and the node nb corresponding to the instant pixel will be set as low. Accordingly, the low cost represents the close relationship between respective nodes.

The graph cut processing element 16 repeatedly divides the connection line while keeping the low cost connection lines. For example, referring to the embodiment of FIGS.

18(A),(B), the node n2 is disconnected from the node n on the right and the node nb and then the corresponding pixel a is judged as belonging to the metal piece. The graph cut element 16 executes such assignment as to the node n on all nodes n and generates the map Ma presented by the binarization image, which is representing the result of the assignment. The map Ma exactly represents the distribution of the metal piece relative to the original image P0.

Tomographic Image Generation Element

Next, the inventor sets forth the tomographic image generation element 23 by superimposing the original image P0. The tomographic image generation element 23 of Embodiment 1 refers not only to the original image P0 but also to the above described map Ma on the operation thereof. According to the description as to the principal of the tomographic image generation referring to FIG. 3, the tomographic image can be generated if the tomographic image generation element 23 superimposes 74 original images P0. Accordingly, if only generation of tomographic image is expected, no generation of the map Ma by the image processing device 22 is needed.

However, if the original image P0 should be simply superimposed, the tomographic image having a false image can be only obtained. Because each original image P0 is incorporating the metal piece. The metal piece thereof cannot be fully obfuscated by superimposition of the original image P0 because of the extreme pixel value. Accordingly, a residual image of the metal piece that cannot be completely canceled by superimposition of images may appear in the periphery of the metal piece of the tomographic image. The residual image thereof is the real identity of the false image appeared in the tomographic image.

Figure 19A:
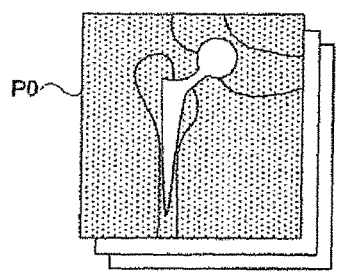
FIGS. 19(A),(B) are schematic diagrams illustrating an operation of the tomographic image generation element of Embodiment 1.
Figure 19B:
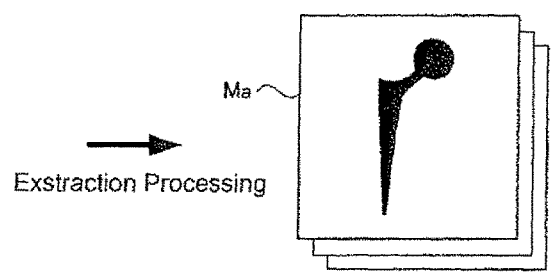
Figure 21A:
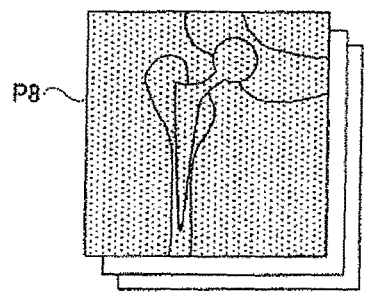
FIGS. 21(A) (B) are schematic diagrams illustrating an operation of the tomographic image generation element of Embodiment 1.
Figure 21B:
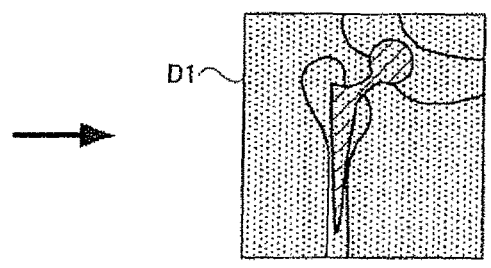

The X-ray tomographic device of Embodiment 1 is a device in which such false image of the tomographic image would not take place. Specifically, the X-ray tomographic device of Embodiment 1 is the device in which no false image appears in the tomographic image by superimposing the metal piece based on the function of the image processing device 22. Specifically, the tomographic image according to Embodiment 1 cannot be generated by superimposing as-is the original image P0. Specifically, referring to FIGS. 19(A),(B), the tomographic image is generated by the tomographic image generation element 23 referring to the map Ma in which the metal piece is extracted from each of the original image P0. The map Ma is generated by that the image processing device 22 executes the extraction processing of the metal piece relative to each of 74 original images P0. Accordingly, 74 maps Ma will be generated Operation of the Tomographic Image Generation Element 23: Metal Piece Cancel Processing The tomographic image generation element 23 generates the tomographic image referring to the map Ma generated by the image processing device 22. The mode thereof is specifically set forth. First, the tomographic image generation element 23 executes the image processing so as to cancel the image of the metal piece incorporated into each of the original images P0. Specifically, referring to FIGS. 20 (A), (B), (C), the tomographic image generation element 23 understands the position/size/range of the metal piece incorporated into the original image P0 by referring to the map Ma. And the tomographic image generation element 23 converts the pixel value of pixels inside metal piece to the pixel value of pixels in the periphery of the metal piece. Then, the pixel value related to the conversion is e.g. an average value of pixels in the periphery of the metal piece. In such mode, the metal piece cancel image P8 can be generated as if the metal piece incorporated into the original image P0 is assimilated in the periphery. The metal piece cancel image P8 is generated corresponding to each of 74 original images P0. Accordingly, the image processing device 23 performs the metal piece cancel processing, wherein a metal piece cancel image P8 is generated by canceling the metal piece incorporated into the original image P0 from the original image P0, referring to the map Ma in which the metal piece is extracted from each original image P0 continuously imaged while changing the imaging direction relative to the subject M, Operation of the Tomographic Image Generation Element 23: Generation of the Metal Piece Cancel Tomographic Image Referring to FIGS. 21 (A),(B), the tomographic image generation element 23 generates the tomographic image by superimposing 74 metal piece cancel images P8. The image generated at this time is called as the metal piece cancel tomographic image D1 for discrimination purpose. The metal piece cancel tomographic image D1 is generated by superimposing the images as if the metal piece assimilated with the periphery of the metal piece so that no false image will appear in the periphery of the metal piece. However, the region corresponding to the metal piece illustrated in the inclination region of the metal piece cancel tomographic image D1 in FIGS. 21(A),(B) is completely filled up with incorrect pixel value. Because, the pixel value of the pixel inside the metal piece relative to the metal piece cancel image P8 that is a base of the metal piece cancel tomographic image D1 is converted to the pixel value different from the right pixel value. Hereafter, the tomographic image generation element 23 is operative to bring the pixel value of the metal piece region relative to the metal piece cancel tomographic image D1 closer to the right pixel value. The tomographic image generation element 23 performs the metal piece cancel tomographic image generation processing that generates the metal piece cancel tomographic image D1 by superimposing a plurality of the metal piece cancel image P8, Operation of the Tomographic Image Generation Element 23: Metal Piece Trimming Processing Specifically, the tomographic image generation element 23 performs a different image processing on the 74 original images P0. Referring to FIG. 22, the tomographic image generation element 23 subtracts the corresponding metal piece cancel image P8 from each of the original image P0. The original image P0 and the metal piece cancel image P8 have the same image as the region other than the metal piece so that the same regions are canceled and erased by the subtraction processing. Specifically, the trimming image P9 is generated as if the region corresponding to the metal piece is trimmed from each of the original image P0 by the subtraction processing with the tomographic image generation element 23. The trimming image P9 is more different than the above map Ma that might first be surmised similar. The map Ma is a binarization image and represents the aspect of the metal piece on the original image P0 but, on the other hand, the trimming image P9 represents not only the aspect of the metal piece but also light and shade inside the metal piece. Specifically, the metal piece of the trimming image P9 looks like a thinner metal piece incorporated into the original image P0. Because, when respective images are subject to subtraction processing, the pixel value (pixel value of pixels in the periphery of the metal piece relative to the original image P0) of the metal piece of the metal piece cancel image P8 is subtracted from the pixel value of pixels on the metal piece of the original image P0. Accordingly, the tomographic image generation element 23 performs the metal piece trimming processing that generates a trimming image P9 by taking out the corresponding regions to the metal piece from each of original image referring to the map Ma.

Figure 23A:
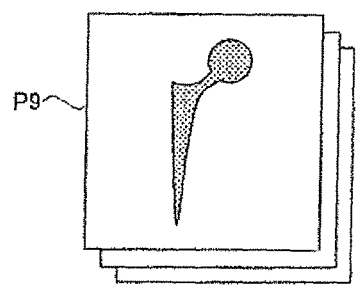
FIGS. 23(A),(B) are schematic diagrams illustrating an operation of the tomographic image generation element of Embodiment 1.
Figure 23B:
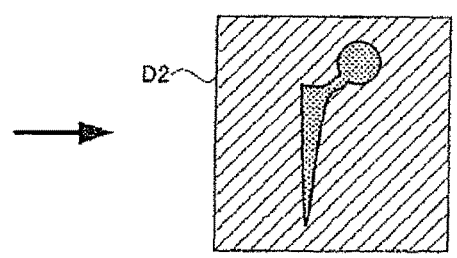

Operation of the Tomographic Image Generation Element 23: Generation of Metal Piece Tomographic Image Referring to FIGS. 23(A), (B), the tomographic image generation element 23 generates the tomographic image by superimposing 74 trimming images P9. The image generated at this time is called as the metal piece tomographic image D2 for image discrimination purpose. The metal piece tomographic image D2 is the tomographic image that shares the slice section with the metal piece cancel tomographic image D1 Further, the metal piece tomographic image D2 is generated by superimposing the image into which the only metal piece is incorporated so that the tomographic image of the metal piece can be incorporated. Accordingly, referring to FIGS. 23(A), (B), the region corresponding to the periphery of the metal piece, illustrated as the inclination region of the metal piece tomographic image D2, is not imaged at all. Accordingly, the tomographic image generation element 23 executes the metal piece tomographic image generation processing that generates the metal piece tomographic image D2 by superimposing a plurality of the trimming image P9.

Figure 24A:
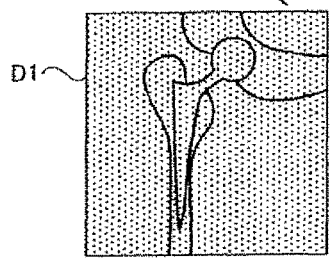
FIGS. 24(A),(B),(C) are schematic diagrams illustrating an operation of the tomographic image generation element of Embodiment 1.
Figure 24B:
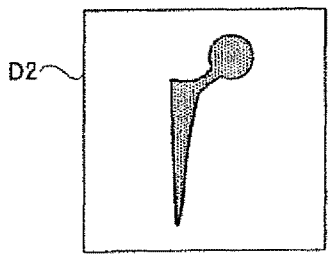
Figure 24C:
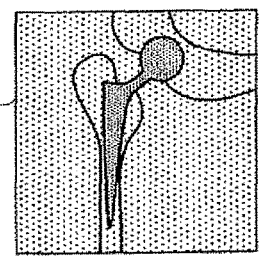

Operation of the Tomographic Image Generation Element 23: Addition of the Tomographic Image Accordingly, the tomographic image generation element 23 generates the tomographic images in two different systems. Referring to the last FIGS. 24(A), (B), the tomographic image generation element 23 performs the addition of the tomographic image D1, D2 thereof. The image generated at this time is called as the synthetic tomographic image D3 for image discrimination purpose. The synthetic tomographic image D3 provides a superior visual recognition. Specifically, regions other than the metal piece of the synthetic tomographic image D3 is originated in the metal piece trimming tomographic image D1 so that no false image can appear. Then, the metal piece region of the synthetic tomographic image D3 is originated in the metal piece tomographic image D2 so that the reliability of the pixel value can be high. Accordingly, the tomographic image generation element 23 generates the synthetic tomographic image D3 by adding the metal piece trimming tomographic image D1 and the metal piece tomographic image D2. The synthetic tomographic image D3 is displayed on the display 27 and then the operation of Embodiment 1 can be completed.

According to the composition of the present invention, the metal piece incorporated into the original image can be assuredly extracted based on the composition. That is, the image processing device 22 of the present invention generates the standard deviation image P1 in which the standard deviation is mapped relative pixels constituting the original image, and then generates the subtraction image P2 by addition or subtraction of the original image and the standard deviation image P1, and further extracts the metal piece by the binarization of the subtraction image thereof. In the certain subtraction image P2, the image of the structure appearing in the region other than the metal piece of the original image is erased. Accordingly, the structure other than e.g., the metal piece incorporated whity on the original image will not appear in the subtraction image. Accordingly, if the binarization processing capable of extracting e.g., the metal piece incorporated whity in the subtraction image P2 is added, an accurate graph cut processing can be performed so that an image originated in the structure other than the metal piece in the result image will never appear.

The present invention is not limited to the above system and further following alternative Embodiment can be implemented.

(1) The above image processing device 22 having the image subtraction element 12 comprises the subtraction image P2 by subtraction the standard deviation image P1 from the original image P0 because the metal piece m0 is whity and shows up relative to the original image P0 in the above Embodiment. Specifically, the above Embodiment is effective in the case of that the pixel of the metal piece m0 relative to the original image P0 has the high pixel value.

In the different case from the above Embodiment and the case of the metal piece m0 showing up dark, the image addition element instead of the image subtraction element 12 can be more effective. The image addition element is the system that generates the addition image by addition of the original image P0 and the standard deviation image P1. When the addition image is generated, the pixel value is added largely in the region near the profile of the metal piece m0 of the original image P0 and the region in which the dark structure other than the metal piece is incorporated. Accordingly, the addition image is the image in which the region that is surely the metal piece and the region other than the metal piece can be easily separated. Given the addition image is binarized, the same image as the binarization subtraction image P3 set forth in Embodiment 1 can be obtained.

INDUSTRIAL APPLICABILITY

As set forth above, the image processing device of the present invention is suitable for medicinal field.

EXPLANATION OF REFERENCES

P Standard deviation image
P2 Subtraction image (Calculation image)
P3 Binarization subtraction image (Binarization calculation image)
P4 Profile extraction image
11 Standard deviation image generation element (standard deviation image generation means)
12 Image subtraction element (Image calculation means)
13 Binarization element (Calculation image binarization means)
14 Profile extraction element (Profile extraction means)
15 Snake processing element (Snake processing means)
16 Graph cut processing element (Graph cut processing means)
23 Tomographic image generation element (Tomographic image generation means)

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

The invention claimed is:

1. An image processing device, that executes an image processing on an original image incorporating a metal piece obtained by the radiation imaging of a subject having an implanted metal piece inside, comprises:

a standard deviation image generation module operative to generate a standard deviation image, wherein the standard deviation is mapped relative to the pixels constituting said original image by repeating an operation to calculate the standard deviation of the pixel values of an attention pixel of said original image and the periphery of said attention pixel while changing said attention pixel;

an image calculation module operative to generate a calculation image by addition or subtraction between said original image and said standard deviation image;

a calculation image binarization module operative to generate the binarization calculation image by binarization of said calculation image;

a graph cut processing module that is operative to comprehend the distribution of the metal piece on the original image based on said binarization calculation image, obtain the representative value of pixel values of the metal piece region of said original image and the representative value of pixel values of the region other than the metal piece, and generate a map showing the distribution of the metal piece relative to said original image by execution of the graph cut processing on said original image referring to each representative value.

2. The image processing device, according to claim 1, further comprising:

a tomographic image generation means module that is operative to execute the steps of:

a metal piece cancel processing that generates a metal piece cancel image by canceling the metal piece incorporated into said original image from each said original image continuously imaged while changing the imaging direction relative to the subject referring to said map;

a metal piece cancel tomographic image generation processing that generates metal piece cancel tomographic image by superimposing a plurality of said metal piece cancel image;

a metal piece trimming processing that generates a trimming image by taking out the corresponding region to the metal piece from each said original image referring to said map;

a metal piece tomographic image generation processing that generates a metal piece tomographic image by superimposing a plurality of said trimming images; and a tomographic image addition processing so as to generate the synthetic tomographic image by addition of said metal piece cancel tomographic image and the metal piece tomographic image.

3. A radiographic device, according to claim 1, further comprising;

a radiation source that irradiates a radiation;

a detection module that is operative to detect the radiation transmitted through the subject; and an image generation module that is operative to generate the original image based on the detection signal of said detection module.

\* \* \* \* \*